United States Patent
Coenen et al.

(10) Patent No.: US 6,562,167 B2
(45) Date of Patent: May 13, 2003

(54) METHODS FOR MAKING GARMENTS WITH FASTENING COMPONENTS

(75) Inventors: Joseph Daniel Coenen, Kaukauna, WI (US); Jack Lee Couillard, Menasha, WI (US); Robert Lee Popp, Hortonville, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 112 days.

(21) Appl. No.: 09/855,484

(22) Filed: May 15, 2001

(65) Prior Publication Data

US 2002/0000291 A1 Jan. 3, 2002

Related U.S. Application Data

(60) Provisional application No. 60/204,480, filed on May 16, 2000, and provisional application No. 60/204,407, filed on May 16, 2000.

(51) Int. Cl.[7] .............................................. B32B 31/16
(52) U.S. Cl. ...................... 156/73.1; 156/269; 156/290; 156/308.4
(58) Field of Search ............................... 156/73.1, 267, 156/269, 290, 308.2, 308.4

(56) References Cited

U.S. PATENT DOCUMENTS

| | | |
|---|---|---|
| 1,912,466 A | 6/1933 | Remington |
| 1,912,724 A | 6/1933 | Remington |

(List continued on next page.)

FOREIGN PATENT DOCUMENTS

| | | |
|---|---|---|
| EP | 0 217 032 A2 | 4/1987 |
| EP | 0 320 989 A2 | 6/1989 |
| EP | 0 532 486 A1 | 3/1993 |
| EP | 0 631 766 A1 | 1/1995 |
| EP | 0 689 816 A2 | 1/1996 |
| EP | 0 753 292 A2 | 1/1997 |
| EP | 0 761 193 A2 | 3/1997 |
| EP | 0 800 808 A1 | 10/1997 |
| EP | 0 803 602 A1 | 10/1997 |
| EP | 0 820 747 A1 | 1/1998 |
| EP | 0 934 739 A2 | 8/1999 |
| FR | 2 299 254 | 8/1976 |
| GB | 1 384 622 | 2/1975 |
| GB | 1 593 600 | 7/1981 |
| GB | 2 160 817 A | 1/1986 |
| GB | 2 288 314 A | 10/1995 |
| WO | WO 91/19613 A1 | 12/1991 |
| WO | WO 95/18589 A1 | 7/1995 |
| WO | WO 95/18591 A2 | 7/1995 |
| WO | WO 95/27462 A1 | 10/1995 |
| WO | WO 95/32639 A1 | 12/1995 |

(List continued on next page.)

Primary Examiner—James Sells
(74) Attorney, Agent, or Firm—Thomas M. Gage

(57) ABSTRACT

Efficient high speed methods for making garments with fastening components include positioning first fastening components on one surface of a product assemblage on opposite sides of a machine center line at selected first cross machine direction locations. In particular embodiments, second fastening components are positioned on another surface of the product assemblage on opposite sides of the machine center line at selected second cross machine direction locations. The product assemblage can be processed through bonding devices disposed at selected cross machine direction locations to bond the fastening components to opposite surfaces of the product assemblage. In other embodiments, the product assemblage can be processed through bonding devices subsequent to positioning the first fastening components. The bonding devices can bond the first fastening components to particular zones of side panel strips and form second fastening components comprising discontinuous nonadhesive bonds in other zones of the side panel strips.

48 Claims, 7 Drawing Sheets

U.S. PATENT DOCUMENTS

| | | | |
|---|---|---|---|
| 2,037,561 A | 4/1936 | Blosser et al. | |
| 2,114,124 A | 4/1938 | Horton | 270/76 |
| 2,714,230 A | 8/1955 | Young | |
| 3,116,920 A | 1/1964 | Geer et al. | |
| 3,502,322 A | 3/1970 | Cran | |
| 3,632,030 A | 1/1972 | Cohn et al. | |
| 3,808,767 A | 5/1974 | Reid | |
| 3,870,292 A | 3/1975 | Bradley | |
| 3,874,043 A | 4/1975 | Holm | |
| 3,918,706 A | 11/1975 | Craft | |
| 3,994,486 A | 11/1976 | Nystrand | |
| 4,018,432 A | 4/1977 | Frick | |
| 4,053,967 A | 10/1977 | Mair | |
| 4,170,347 A | 10/1979 | Lewis | |
| 4,186,860 A | 2/1980 | Reba | |
| 4,197,621 A | 4/1980 | Mair | |
| 4,279,610 A | 7/1981 | Reba | |
| 4,323,534 A | 4/1982 | DesMarais | |
| 4,342,413 A | 8/1982 | Reba | |
| 4,418,513 A | 12/1983 | Plahm | |
| 4,453,709 A | 6/1984 | Reba | |
| 4,479,640 A | 10/1984 | Smith | |
| 4,516,760 A | 5/1985 | Stumpf | |
| 4,543,154 A | 9/1985 | Reiter | |
| 4,597,573 A | 7/1986 | Reba et al. | |
| 4,640,726 A | 2/1987 | Sallee et al. | |
| 4,663,106 A | 5/1987 | Pomplun et al. | |
| 4,663,220 A | 5/1987 | Wisneski et al. | |
| 4,665,306 A | 5/1987 | Roland et al. | |
| 4,702,468 A | 10/1987 | Pollich | |
| 4,704,116 A | 11/1987 | Enloe | |
| 4,710,189 A | 12/1987 | Lash | |
| 4,717,375 A | 1/1988 | Lundmark | |
| 4,750,442 A | 6/1988 | Keeton | |
| 4,808,252 A | 2/1989 | Lash | |
| 4,834,738 A | 5/1989 | Kielpikowski et al. | |
| 4,865,579 A | 9/1989 | Kirby et al. | |
| 4,875,668 A | 10/1989 | Spyra | |
| 4,883,549 A | 11/1989 | Frost et al. | |
| 4,885,853 A | 12/1989 | McCabe | |
| 4,936,840 A | 6/1990 | Proxmire | |
| 4,940,464 A | 7/1990 | Van Gompel et al. | |
| 5,046,272 A | 9/1991 | Vogt et al. | |
| 5,092,863 A | 3/1992 | Schanzlin | |
| 5,093,422 A | 3/1992 | Himes | |
| 5,104,116 A | 4/1992 | Pohjola | |
| 5,110,403 A | 5/1992 | Ehlert | |
| 5,140,757 A | 8/1992 | Terada | |
| 5,176,615 A | 1/1993 | Munsch | |
| 5,184,555 A | 2/1993 | Quadracci et al. | |
| 5,197,722 A | 3/1993 | Adamski, Jr. et al. | |
| 5,199,623 A | 4/1993 | Rajala et al. | |
| 5,224,405 A | 7/1993 | Pohjola | |
| 5,226,992 A | 7/1993 | Morman | |
| 5,300,007 A | 4/1994 | Kober | |
| 5,304,599 A | 4/1994 | Himes | |
| 5,330,598 A | 7/1994 | Erdman et al. | |
| 5,344,691 A | 9/1994 | Hanschen et al. | |
| 5,353,979 A | 10/1994 | Gartmann | |
| 5,363,784 A | 11/1994 | Adamski, Jr. et al. | |
| 5,399,219 A | 3/1995 | Roessler et al. | |
| 5,435,802 A | 7/1995 | Kober | |
| 5,556,360 A | 9/1996 | Kober et al. | |
| 5,660,666 A | 8/1997 | Dilnik et al. | |
| 5,705,013 A | 1/1998 | Nease et al. | |
| 5,765,495 A | 6/1998 | Adamski, Jr. | |
| 5,766,389 A | 6/1998 | Brandon et al. | |
| 5,779,831 A | 7/1998 | Schmitz | |
| 5,788,805 A | 8/1998 | Herrmann | |
| 5,795,433 A | 8/1998 | Niedermeyer | |
| 5,797,831 A | 8/1998 | Roberts et al. | 493/438 |
| 5,803,448 A | 9/1998 | Stiel et al. | |
| 5,807,368 A | 9/1998 | Helmer | |
| 5,858,515 A | 1/1999 | Stokes et al. | |
| 5,865,135 A | 2/1999 | Price et al. | |
| 5,904,802 A | 5/1999 | Niedermeyer | |
| 5,915,319 A | 6/1999 | Price et al. | |
| 5,916,203 A | 6/1999 | Brandon et al. | |
| 5,919,334 A | 7/1999 | Niedermeyer | |
| 5,997,981 A | 12/1999 | McCormack et al. | |
| 6,015,934 A | 1/2000 | Lee et al. | 604/358 |
| 6,022,431 A | 2/2000 | Blenke et al. | |
| 6,022,432 A | 2/2000 | Elsberg et al. | |
| 6,027,440 A | 2/2000 | Roth | |
| 6,036,805 A | 3/2000 | McNichols | |
| 6,113,717 A | 9/2000 | Vogt et al. | |
| 6,461,471 B1 | 10/2002 | Tharpe, Jr. et al. | 156/580.1 |

FOREIGN PATENT DOCUMENTS

| | | |
|---|---|---|
| WO | WO 95/33618 A1 | 12/1995 |
| WO | WO 97/23180 A1 | 7/1997 |
| WO | WO 97/24098 A1 | 7/1997 |
| WO | WO 98/15248 A1 | 4/1998 |
| WO | WO 99/65441 A1 | 12/1999 |
| WO | WO 00/35395 A2 | 6/2000 |
| WO | WO 00/37009 A2 | 6/2000 |

METHODS FOR MAKING GARMENTS WITH FASTENING COMPONENTS

This application claims the benefit of Provisional application Ser. No. 60/204,480, filed May 16, 2000 and No. 60/204,407, filed May 16, 2000.

Background of the Invention

The present invention pertains to methods for making garments with fastening components, and more particularly to methods for making disposable absorbent articles with mechanical fastening components.

Garments such as disposable absorbent garments have numerous applications including diapers, training pants, feminine care products, and adult incontinence products. The typical disposable absorbent garment is formed as a composite structure including an absorbent assembly disposed between a liquid permeable bodyside liner and a liquid impermeable outer cover. These components can be combined with other materials and features such as elastic materials and containment structures to form a product that is specifically suited to its intended purposes.

One form of disposable absorbent garment is a two-dimensional product that has open sides. Two-dimensional products, such as conventional diapers and some adult incontinence products, are generally flat and provided in an unfastened configuration. These garments have typically included fasteners such as adhesive tape fasteners or hook and loop type fasteners that releasably connect the front and back waist portions to secure the product about the wearer. Two-dimensional products can be easily applied or removed while the wearer is lying down.

Another form of disposable absorbent garment is a three-dimensional product with closed sides so that the product has a unitary waist opening and two leg openings. The wearer raises and lowers the garment to apply the product. Three-dimensional products are particularly appealing because the pant has a very garment-like look. This can be a significant consideration, for example, with children who prefer to wear training pants that look like adult underwear rather than diapers, and with adults who prefer the normalcy of a pant product rather than an incontinence product that must be applied in another fashion.

In addition, prefastened and refastenable disposable absorbent garments have recently been proposed to provide the advantages of both two-dimensional and threedimensional products. Prefastened and refastenable products can be applied and/or removed either like a conventional diaper or like a conventional training pant. For use as training pants, for example, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied like either a diaper or a pant permits the interior of the product to be easily checked without having to pull the product downward.

Disposable absorbent products incorporating fastening components present many manufacturing challenges. In part, this is due to the high speed that is necessary to economically produce relatively low cost disposable absorbent products. The challenges are particularly significant for prefastened and refastenable garments. Such products must be assembled in a manner that allows the fastening components to be properly aligned and engaged. Improperly attached or aligned fasteners can lead to many product deficiencies, including machine waste and/or delay, improper fit, fastener delamination during use, fastener disengagement during use, skin irritation, or the like.

Thus, what is lacking and needed in the art are improved methods for making garments with fastening components, and in particular disposable absorbent articles with mechanical fastening components, where such methods are compatible with the manufacture of prefastened and refastenable garments.

SUMMARY OF THE INVENTION

In response to the above-referenced unfulfilled need in the art, new methods for making garments with fastening components have been discovered. The methods are particularly suited for the manufacture of disposable absorbent articles with mechanical fastening components. In one embodiment, a method of making garments with fastening components, comprises: transporting a continuous product assemblage in a machine direction, the product assemblage defining opposite first and second major surfaces; positioning first fastening components on the first major surface, the first fastening components disposed on opposite sides of a machine center line, the first fastening components disposed at selected first cross machine direction locations; positioning second fastening components on the second major surface, the second fastening components being refastenably engageable with the first fastening components, the second fastening components disposed on opposite sides of the machine center line, the second fastening components disposed at selected second cross machine direction locations; subsequent to positioning the first and second fastening components, processing the product assemblage through a pair of bonding devices, the bonding devices disposed on opposite sides of the machine center line, each bonding device defining an operative bonding width, the bonding devices disposed at selected cross machine direction locations such that the operative bonding widths overlap at least part of the first cross machine direction locations and at least part of the second cross machine direction locations; activating each bonding device such that each bonding device bonds both a first fastening component to the product assemblage and a second fastening component to the product assemblage; and cutting the product assemblage at spaced locations to form a plurality of discrete garments with fastening components.

In another embodiment, a method of making garments with fastening components comprises: transporting a continuous product assemblage in a machine direction, the product assemblage defining a longitudinal center line and opposite first and second major surfaces, the product assemblage comprising a plurality of pairs of opposed side panel strips, each pair comprising a side panel strip extending transversely outward from the longitudinal center line on both sides of the longitudinal center line, the plurality of pairs of opposed side panel strips being spaced from one another in the machine direction; positioning first fastening components on the first major surface of each pair of opposed side panel strips, the first fastening components disposed on opposite sides of the longitudinal center line, the first fastening components disposed at selected first cross machine direction locations; positioning second fastening components on the second major surface of each pair of opposed side panel strips, the second fastening components being refastenably engageable with the first fastening components, the second fastening components disposed on opposite sides of the longitudinal center line, the second fastening components disposed at selected second cross machine direction locations, the second fastening components being spaced in the machine direction from the first fastening components; subsequent to positioning the first and second fastening components, processing the product assemblage through a pair of bonding devices, the bonding devices disposed on opposite sides of the machine center line, each bonding device defining an operative bonding width, the bonding devices disposed at selected cross machine direction locations such that the operative bonding widths overlap at least part of the first cross machine direction locations and at least part of the second cross machine direction locations; activating each bonding device such that each bonding device bonds both a first fastening component to the side panel strips and a second fastening component to the side panel strips; and cutting the product assemblage through each pair of opposed side panel strips to form a plurality of discrete garments, each discrete garment defining a first waist region comprising opposed side panels, a second waist region comprising opposed side panels, and an interconnecting region disposed between and interconnecting the first and second waist region, the first fastening components disposed on the side panels in the first waist region, and the second fastening components disposed on the side panels in the second waist region.

A further embodiment of a method of making garments with fastening components comprises: transporting a continuous product assemblage in a machine direction, the product assemblage defining a longitudinal center line, the product assemblage comprising a plurality of pairs of opposed side panel strips, each pair comprising a side panel strip extending transversely outward from the longitudinal center line on both sides of the longitudinal center line, the plurality of pairs of opposed side panel strips being spaced from one another in the machine direction, each side panel strip defining a leading edge, a leading zone disposed adjacent the leading edge, a trailing edge spaced from the leading edge in the machine direction, and a trailing zone disposed between the trailing edge and the leading zone; positioning first fastening components on each pair of opposed side panel strips, the first fastening components disposed in one of the leading zone or the trailing zone, the first fastening components disposed on opposite sides of the longitudinal center line, the first fastening components disposed at selected first cross machine direction locations; subsequent to positioning the first fastening components, processing the product assemblage through a pair of bonding devices, the bonding devices disposed on opposite sides of the machine center line, each bonding device defining an operative bonding width, the bonding devices disposed at selected cross machine direction locations such that the operative bonding widths overlap at least part of the first cross machine direction locations; activating each bonding device such that each bonding device bonds a first fastening component to the side panel strips and each bonding device forms a second fastening component in the other of leading zone or the trailing zone, each second fastening component comprising a discrete portion of the other of the leading zone or the trailing zone having discontinuous nonadhesive bonds formed therein, the discrete portions being refastenably engageable with the first fastening components, the discrete portions disposed at selected second cross machine direction locations which overlap at least part of the first cross machine direction locations; and cutting the product assemblage through each pair of opposed side panel strips between the leading and trailing zones to form a plurality of discrete garments, each discrete garment defining a first waist region comprising opposed side panels, a second waist region comprising opposed side panels, and an interconnecting region disposed between and interconnecting the first and second waist region, the first fastening components disposed on the side panels in the first waist region, and the second fastening components disposed on the side panels in the second waist region.

Fastening components to form refastenable seams can comprise separate elements bonded to another component of the pant. Alternatively, the fastening components can comprise a portion of another element of the pant, such as the bodyside liner, the outer cover, separate side panels if employed, integral side panels if employed, a belt-type component extending transversely across the chassis if employed, or the like. Thus, unless otherwise specified, the term "fastening component" includes separate components which function as fasteners and regions of materials such as side panels, liners, outer covers or the like which function as fasteners. Moreover, a single material can define multiple fastening components to the extent that different regions of the material function as separate fasteners. The fastening components can be located on the side panels, between the side panels such as on the absorbent chassis, or a combination of the two. The fastening components can have any desired shape, such as square, rectangular, round, curved, oval, irregularly shaped, or the like. Each fastening component can comprise a single fastening element or multiple fastening elements.

The fastening components can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

Refastenable fastening systems allow for easy inspection of the interior of the pant-like product. If necessary, the fastening system also allows the pant to be removed quickly and easily. This is particularly beneficial when the pant contains messy excrement. For training pants, the caregiver can completely remove the pant-like product and replace it with a new one without having to remove the child's shoes and clothing.

The present invention can be used in the manufacture of a wide variety of absorbent and non-absorbent products, including training pants, swim pants, diaper pants, incontinence garments, feminine care products, health care garments, apparel for institutional, industrial and consumer use, or other garments. Absorbent articles are adapted to be worn adjacent to the body of a wearer to absorb and contain various exudates discharged from the body. The absorbent articles can be prefastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

Particular training pants suitable for use with the present invention are disclosed in U.S. Pat. application Ser. No. 09/444,083, filed on Nov. 22, 1999 (corresponding to PCT application WO 00/37009 published Jun. 29, 2000) by A. Fletcher et al. and titled "Absorbent Articles With Refastenable Side Seams;" which is incorporated herein by reference. This reference describes various materials and methods for constructing training pants. Training pants can also be constructed using the methods and apparatus disclosed in U.S. Pat. 4,940,464 issued Jul. 10,1990 to Van Gompel et al.; and U.S. Pat. 5,766,389 issued Jun. 16, 1998 to Brandon et al.; which are also incorporated herein by reference.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The methods and apparatus of the present invention can be used to make a variety of garments that include fastening components. Examples of such garments include disposable absorbent articles such as diapers, training pants, feminine hygiene products, incontinence products, other personal care or health care garments; swim pants; athletic clothing; pants and shorts; or the like. For ease of explanation, the description hereafter will be in terms of methods and apparatus for making a child's training pant. In particular, the methods and apparatus will be described in terms of those for making prefastened disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference.

Figure 1:
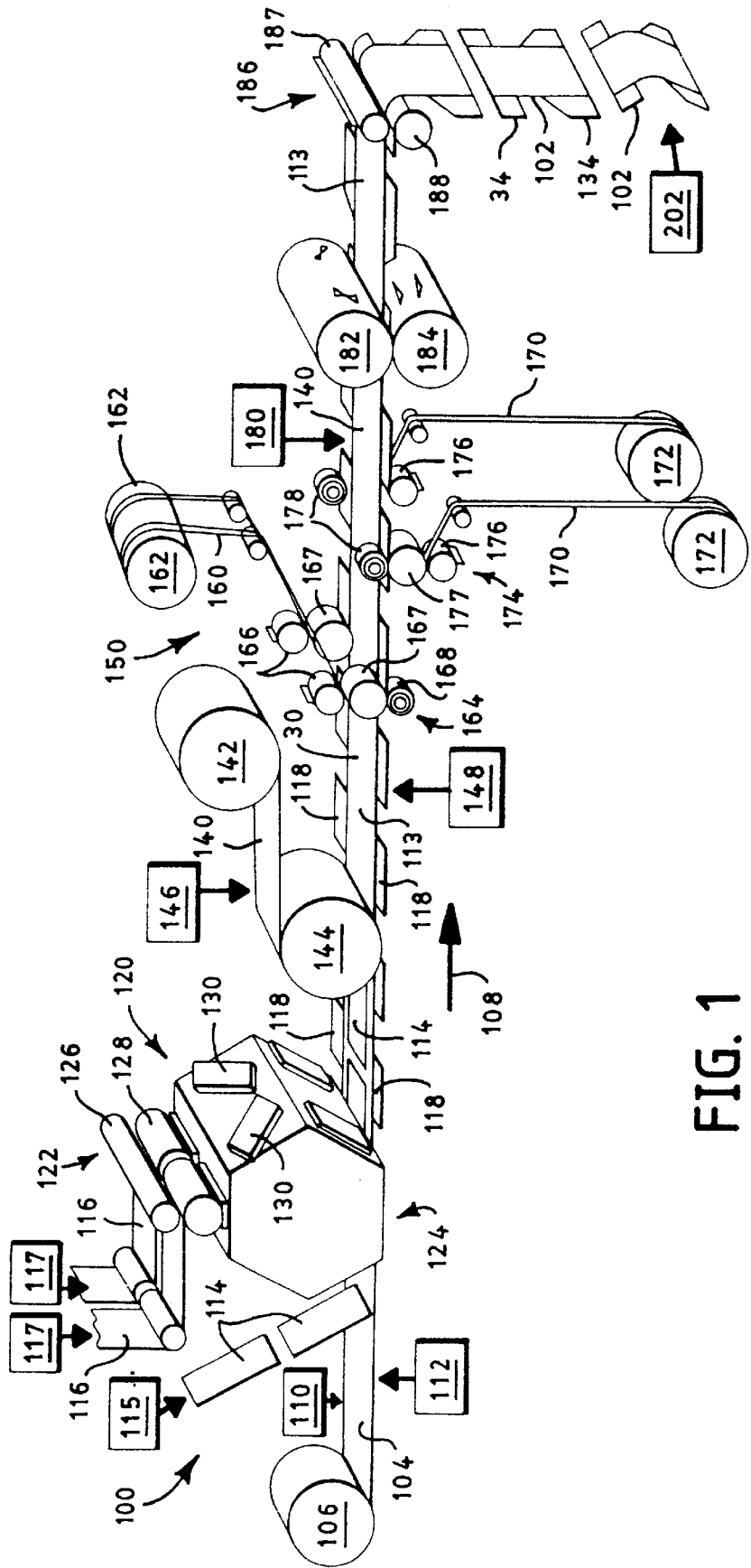
FIG. 1 is a schematic view of one embodiment of a method and apparatus for making garments with fastening components according to the present invention.

FIG. 1 representatively illustrates one embodiment of a method and apparatus for making a training pant 20. The training pant 20 is illustrated separately and in a partially fastened condition in FIG. 4. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 5 and 6, the absorbent chassis 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

Figure 4:
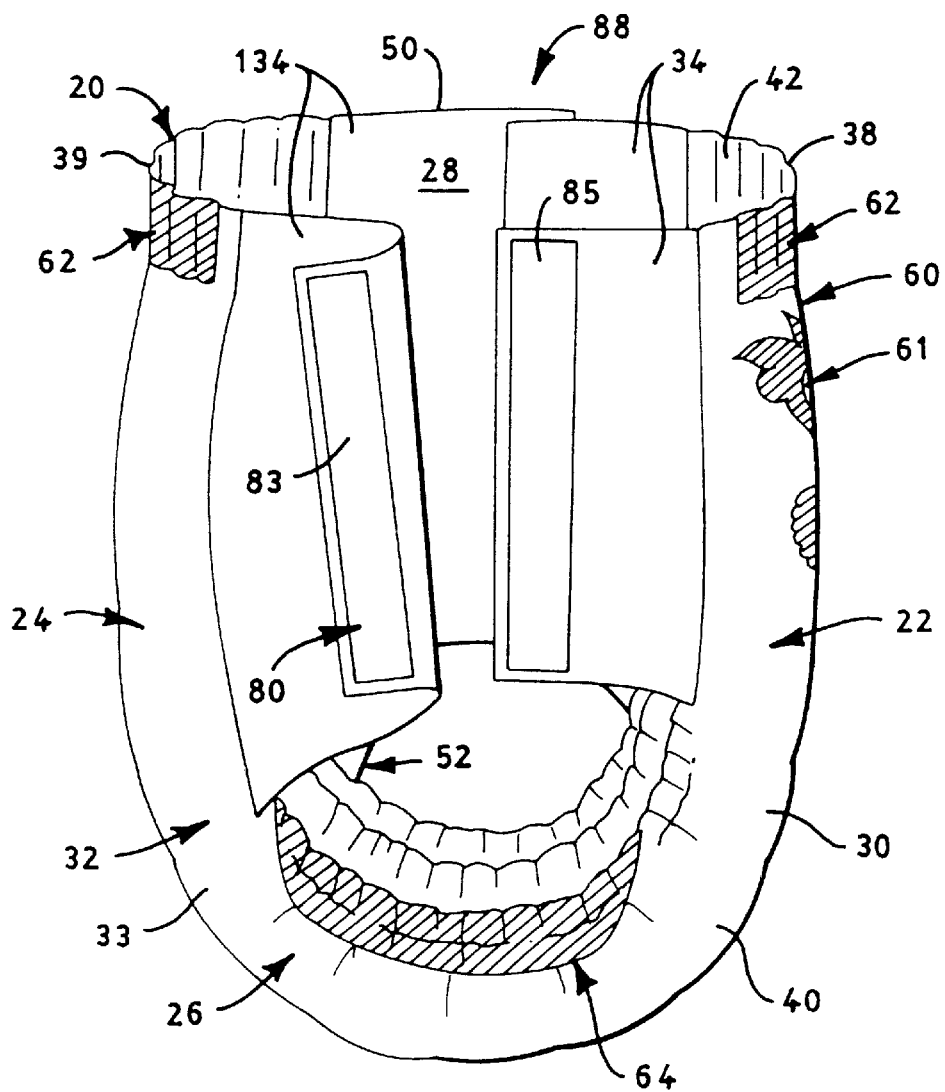
FIG. 4 illustrates a side view of a training pant made by the method and apparatus shown in FIG. 1, where the fastening system is shown engaged on one side of the training pant and disengaged on the other side of the training pant.
Figure 5:
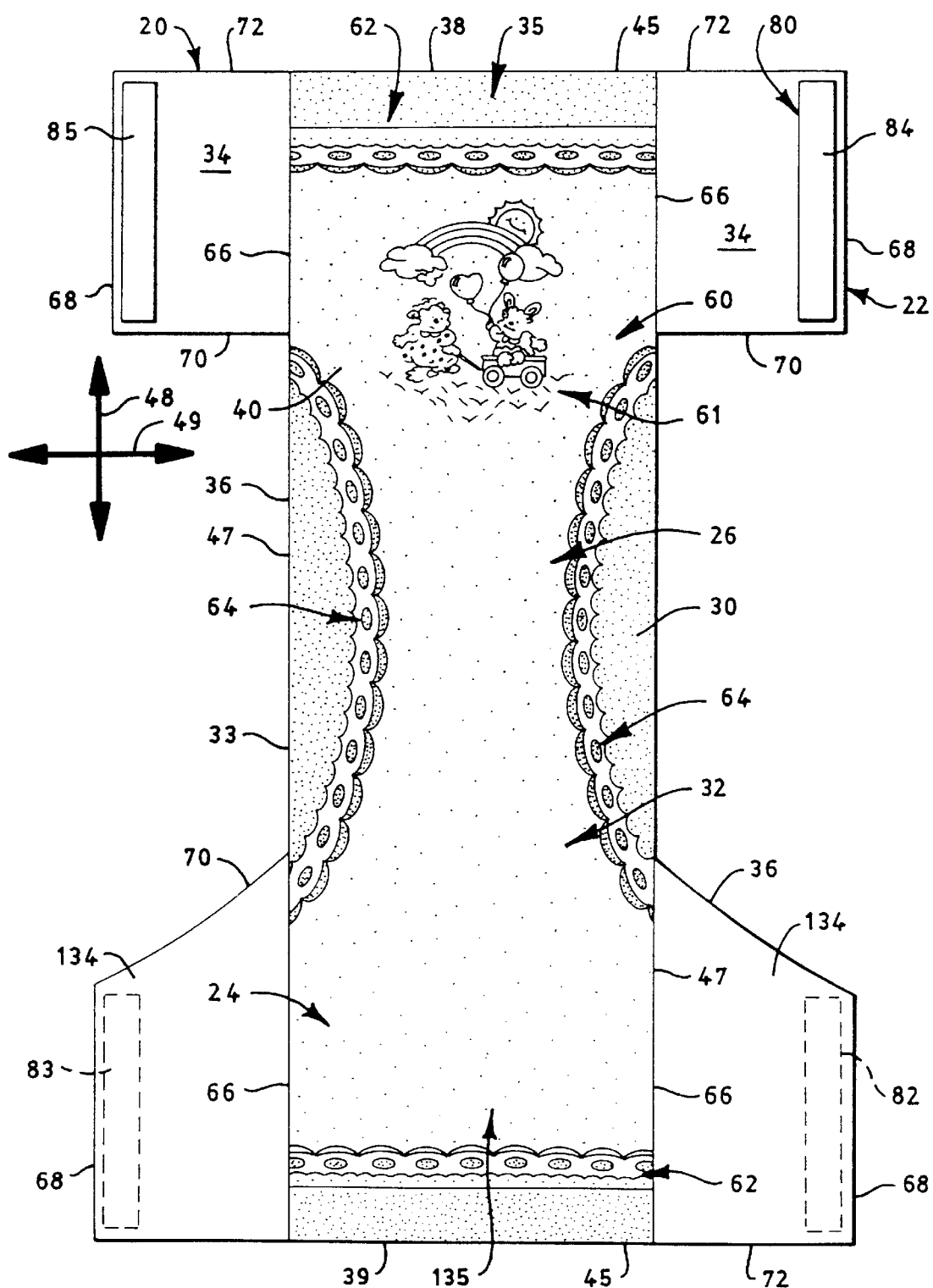
FIG. 5 illustrates a plan view of the training pant shown in FIG. 4 in an unfastened, stretched and laid flat condition, and showing the surface of the training pant that faces away from the wearer.
Figure 6:
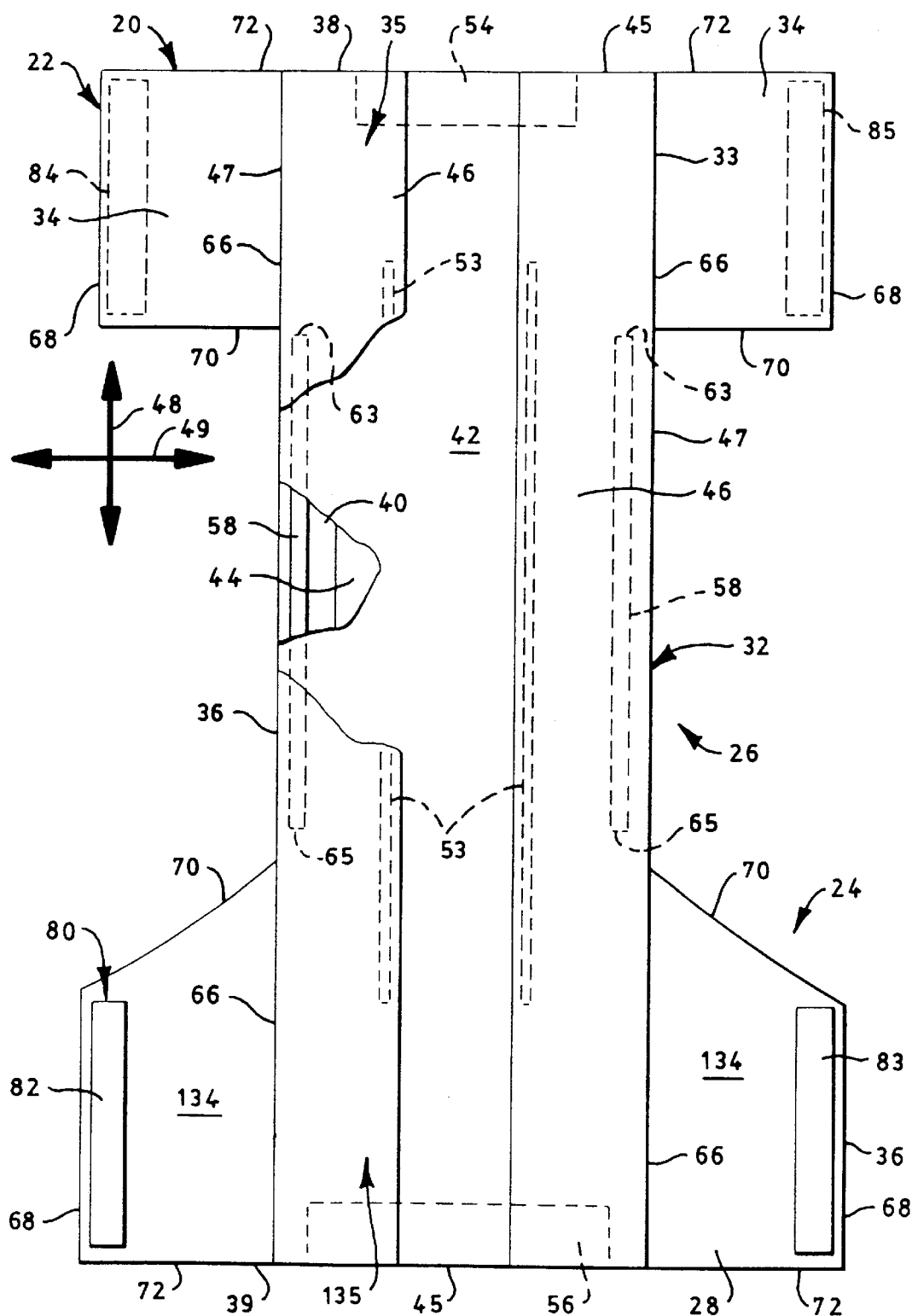
FIG. 6 illustrates a plan view similar to FIG. 5, but showing the surface of the training pant that faces the wearer when the training pant is worn, and with portions cut away to show the underlying features.

The illustrated absorbent chassis 32 comprises a composite structure 33 which can be rectangular or any other desired shape, a pair of transversely opposed front side panels 34, and a pair of transversely opposed back side panels 134. The composite structure 33 and side panels 34 and 134 may comprise two or more separate elements, as shown in FIG. 4, or be integrally formed. Integrally formed side panels and composite structure would comprise at least some common materials, such as the bodyside liner, flap composite, outer cover, other materials and/or combinations thereof, and could define a one-piece elastic, stretchable, or nonstretchable pant. The illustrated composite structure 33 comprises an outer cover 40, a bodyside liner 42 (FIGS. 4 and 6) which is connected to the outer cover in a superposed relation, an absorbent assembly 44 (FIG. 6) which is located between the outer cover and the bodyside liner, and a pair of containment flaps 46 (FIG. 6). The illustrated composite structure 33 has opposite linear end edges 45 that form portions of the front and back waist edges 38 and 39, and opposite linear side edges 47 that form portions of the side edges 36 of the absorbent chassis 32 (FIGS. 5 and 6). For reference, arrows 48 and 49 depicting the orientation of the longitudinal axis and the transverse axis, respectively, of the training pant 20 are illustrated in FIGS. 5 and 6.

With the training pant 20 in the fastened position as partially illustrated in FIG. 4, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent chassis 32 includes the transversely opposed front side panels 34 and a front center panel 35 (FIGS. 5 and 6) positioned between and interconnecting the side panels. The back waist region 24 of the absorbent chassis 32 includes the transversely opposed back side panels 134 and a back center panel 135 (FIGS. 5 and 6) positioned between and interconnecting the side panels. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 6) can be operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 6). The waist elastic members 54 and 56 can be operatively joined to the outer cover 40 and/or bodyside liner 42 along the opposite waist edges 38 and 39, and can extend over part or all of the waist edges. The leg elastic members 58 can be operatively joined to the outer cover 40 and/or bodyside liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material 30 commercially available from Mitsui Toatsu Chemicals, Inc., Tokyo, Japan, or an XKO-8044 polyolefin film commercially available from 3M Company, Minneapolis, Minn. U.S.A.

As shown in FIGS. 4 and 5, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. 5,766,389 issued Jun. 16, 1998 to Brandon et al., which is incorporated herein by reference. The primary pictorial image 61 is desirably positioned in the front waist region 22 along the longitudinal center line of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pennsylvania in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pant can comprise elastomeric or nonelastomeric materials.

The absorbent assembly 44 (FIG. 6) is positioned between the outer cover 40 and the bodyside liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 which can be rectangular or any other desired shape comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded along attachment lines 66 to the composite structure 33 of the absorbent chassis 32 in the respective front and back waist regions 22 and 24. More particularly, as shown best in FIGS. 5 and 6, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover, the bodyside liner, and/or another component of the absorbent chassis. The front and back side panels 34 and 134 can be permanently bonded together or be releasably attached to one another as illustrated by the fastening system 80.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the illustrated back side panels 134 have a continually decreasing length dimension moving from the attachment line 66 to the distal edge 68, as is best shown in FIGS. 5 and 6.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown).

The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. 4,663,220 issued May 5, 1987 to Wisneski et al.; U.S. Pat. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary loop type fasteners. In another particular embodiment, the first fastening components 82 and 83 each comprise loop type fasteners and the second fastening components 84 and 85 each comprise complementary hook type fasteners. Alternatively, the fastening components can comprise interlocking similar surface fasteners; or the like. Although the illustrated embodiments show the back waist region 24 overlapping the front waist region 22, which is convenient, the training pant 20 can also be configured so that the front waist region overlaps the back waist region.

Loop type fasteners typically comprise a fabric or material having a base or backing structure and a plurality of loop members extending upwardly from at least one surface of the backing structure. The loop material can be formed of any suitable material, such as acrylic, nylon, polypropylene or polyester, and can be formed by methods such as warp knitting, stitch bonding or needle punching. Loop type materials can also comprise any fibrous structure capable of entangling or catching hook type materials, such as carded, spunbonded or other nonwoven webs or composites, including elastomeric and nonelastomeric composites. Suitable loop materials are available from Guilford Mills, Inc., Greensboro, N.C. U.S.A. under the trade designation No. 36549. Another suitable loop material can comprise a pattern un-bonded web as disclosed in U.S. Pat. 5,858,515 issued Jan. 12, 1999 to Stokes et al.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82–85 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a unidirectional hook pattern and having a thickness of about 0.5 millimeters (20 mils); and Minnesota Mining & Manufacturing Co., St. Paul, Minn. U.S.A., including specific materials identified as CS-600.

With particular reference to FIG. 6, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 5, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks.

Figure 3:
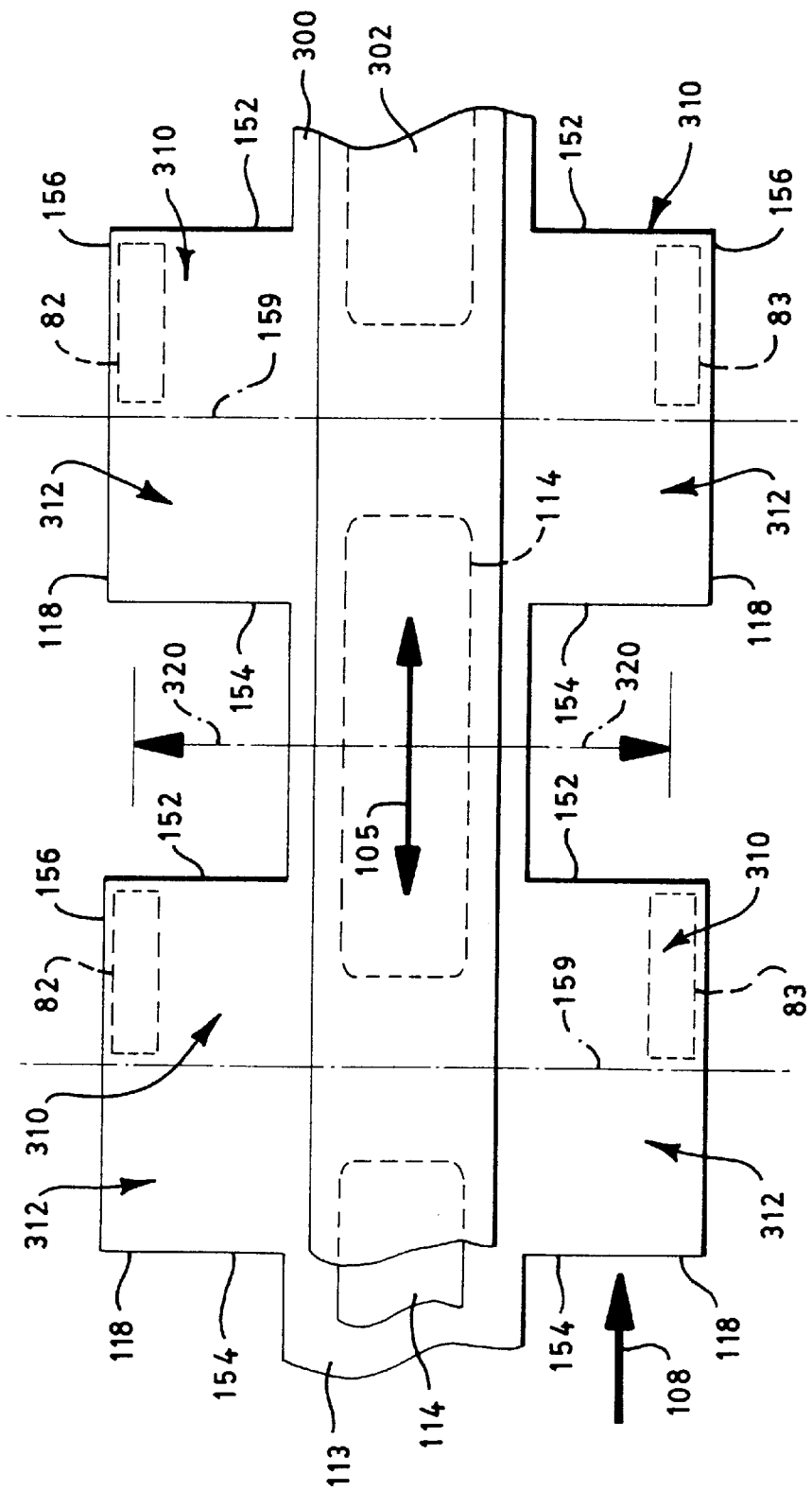
FIG. 3 illustrates a top view of a portion of a product assemblage in an alternative process according to the present invention.

According to one aspect of the present invention, the fastening components 82–85 can be at least partially adhered to or formed in the side panels 34 and 134 with discontinuous nonadhesive bonds. As used herein, the term "discontinuous nonadhesive bonds" refers to a regular or irregular pattern of nonadhesive bonds such as ultrasonic bonds and/or thermal bonds that is spatially discontinuous. The fastening components can comprise separate fastening elements or can comprise distinct regions of an integral material. For example, the training pant 20 can include an integral second fastening material disposed in the front waist region 22 for refastenably connecting to the first fastening components 82 and 83 at two or more different regions, which define the second fastening components 84 and 85 (FIG. 3). In a particular embodiment, the fastening components can comprise integral portions of the waist regions. For instance, one of the elastomeric front or back side panels can function as second fastening components in that they can comprise a material that is releasably engageable with fastening components disposed in the opposite waist region.

The fastening components are desirably rectangular, although they may alternatively be square, round, oval, curved or otherwise non-rectangularly shaped. In particular embodiments, each of the fastening components 82–85 defines a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82–85 are releasably engaged, the side edges 36 of the absorbent chassis 32 in the crotch region 26 define the leg openings 52, and the waist edges 38 and 39 of the absorbent chassis, including the waist end edges 72 of the side panels, define the waist opening 50. For improved formation of the leg openings 52, it can be desirable in some embodiments for the front side panels 34 to be longitudinally spaced from the back side panels 134 (see FIGS. 5 and 6). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82–85 form refastenable seams 88 (FIG. 4) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82–85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the refastenable seams 88 to be located at the sides of the wearer, it can be particularly desirable for the transverse distance between the first fastening components 82 and 83 to be equal to or substantially equal to the transverse distance between the second fastening components 84 and 85. The transverse distance between a set of fasteners is measured parallel to the transverse axis 49 between the longitudinal center lines of the fasteners, measured with the side panels 34 and 134 in an unstretched condition.

One embodiment of an assembly section 100 for making a continuous stream of partially assembled, discrete training pants 102 is illustrated in FIG. 1. The specific equipment and processes used in the assembly section 100 can vary greatly depending on the specific type of garment being manufactured. The particular process and apparatus described in relation to FIG. 1 is specifically adapted to manufacture training pants 20 of the type illustrated in FIG. 4.

The various components of the training pant can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIG. 1. Suitable absorbent supply mechanisms, web unwinds, conveyor systems, registration systems, drives systems, control systems and the like, for use with the present process are disclosed in U.S. Pat. 5,766,389 issued Jun. 16, 1998 to Brandon et al., which is incorporated herein by reference. Also, the outer cover graphics 61 are not shown in FIG. 1.

A continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The continuously moving product assemblage 113 defines a longitudinal center line 105 (FIG. 2) which can correspond to the machine center line. The product assemblage 113 will be cut downstream to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each training pant. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual strips 118, also referred to as side panel strips 118, and positioned partially on the bodyside liner material 104 using an applicator device 120. In the cross machine direction, the individual strips 118 desirably extend laterally outward from the bodyside liner material 104 (see FIGS. 1 and 2) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive garments 102.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips.

As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34 and 134 of the training pant 20 can be provided by portions of the bodyside liner 42 and/or outer cover 40. By any of the foregoing methods, the resulting product assemblage 113 can have a plurality of pairs of opposed side panel strips 118. Each pair has a side panel strip 118 extending transversely outward from the longitudinal center line 105 on each side of the longitudinal center line. The side panel strips 118 forming each pair are at the same machine direction location, and the plurality of pairs of opposed side panel strips, or at least their widest portions, are spaced from one another in the machine direction 108.

A continuous supply of material 140 used to form the outer cover 40 can be provided from a supply roll 142 or other suitable source. The outer cover material 140 can be transported over a laminator roll 144 and married with the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream of the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as are also known to those skilled in the art. Other suitable ultrasonic horns and ultrasonic bonders are commercially available from Branson Sonic Power Company, Danbury, Conn. U.S.A. The bonding devices 148 could otherwise be a thermal or adhesive bonder as are well known.

The continuously moving product assemblage 113 next advances to a fastener application station 150 where fastening components 82–85 are positioned on and bonded to the strips 118 of side panel material 116. The location of the fastening components on the composite is a function in part of the configuration of the assembly section 100. The illustrated assembly section 100 is configured so that the upwardly facing major surface of the product assemblage 113 will become the outer surface 30 of the training pant 20 and the downwardly facing major surface will become the inner surface 28. Moreover, the illustrated assembly section 100 is configured to produce partially assembled training pants 102 having the front waist region 22 of a leading garment connected to the back waist region 24 of a trailing garment. The process could alternatively employ any combination of different orientations. For example, the upwardly facing surface of the product assemblage could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly section 100 could be constructed as a cross-machine direction process wherein the longitudinal axis 48 of each garment could be perpendicular to the machine direction 108 during part or all of the assembly process.

Figure 2:
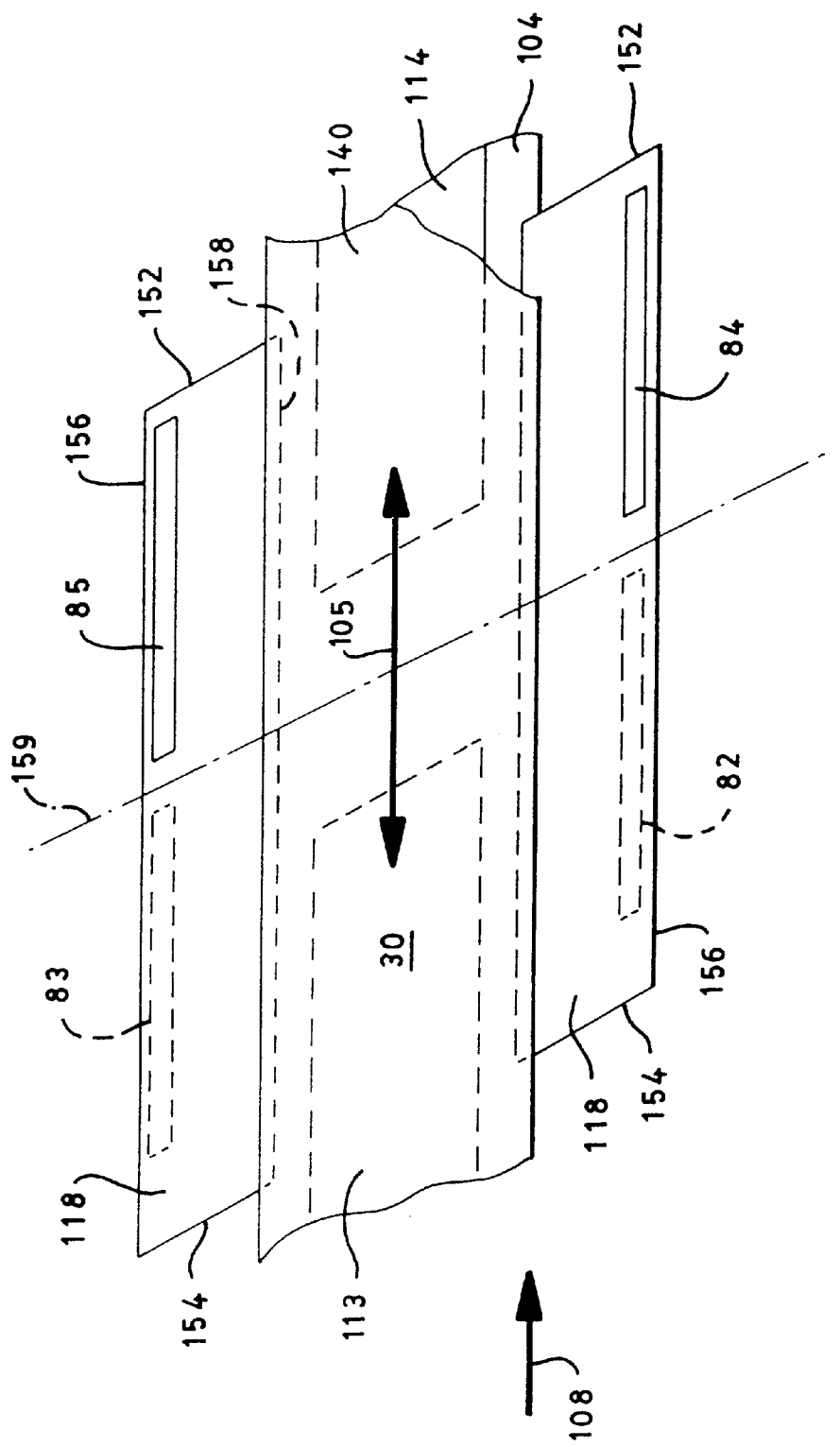
FIG. 2 illustrates a portion of a product assemblage at one point in the process illustrated in FIG. 1.

The location of the fastening components 82–85 in this embodiment is best illustrated in FIG. 2, which shows a portion of the product assemblage 113 which is moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 102. Based on the illustrated orientation of the continuously moving product assemblage 113, the first fastening components 82 and 83 can be positioned on and bonded to the underside of the strips 118 and the second fastening components 84 and 85 can be positioned on and bonded to the top surface of the strips. The first fastening components 82 and 83 can be disposed on opposite sides of the longitudinal center line 105 at selected cross machine direction locations. The second fastening components 84 and 85 can be disposed on opposite sides of the longitudinal center line 105 at the same selected cross machine direction locations as the first fastening components 82 and 83. For purposes of the present invention, the term "cross machine direction location" refers to a location from the machine center line, measured perpendicular to the machine center line. The cross machine direction location of each fastening component 82–85 encompasses the width dimension of the fastening component, where the width dimension is disposed in the cross machine direction.

The first fastening components 82 and 83 can in addition be disposed relatively closer to the trailing edge 154 and the second fastening components 84 and 85 can be disposed relatively closer to the leading edge 152. The first fastening components 82 and 83 can be spaced in the machine direction 108 from the second fastening components 84 and 85 so that the cut line 159 passes therebetween.

With reference again to FIG. 1, continuous webs of second fastener material 160 used to form the second fastening components 84 and 85 can be provided from supply rolls 162 or other suitable sources. The second fastener materials 160 can be cut into individual second fasteners 84 and 85 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 and 83 can be provided from supply rolls 172 or other suitable sources. The first fastener materials 170 can be cut into individual first fasteners 82 and 83 by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

Other arrangements can be used to attach the fastening components 82–85. For example, the fastening components can be applied to the side panel material 116 prior to uniting the side panel material with the bodyside liner material 104 and/or the outer cover material 140; the fastening components can be applied to the bodyside liner material 104 and/or outer cover material 140, whether separate side panels are used or not; portions of other components such as the bodyside liner and/or outer cover can form one or more of the fastening components; the separate side panels or integral side panels can themselves form one or more of the fastening components; the fastening components can be attached as pre-engaged composites 82, 84 and 83, 85; or the like.

After the fastening components are disposed on the strips 118 of side panel material 116, bonding devices 180 can be employed to permanently bond the fastening components to the strips 118. The bonding devices 180 can be adapted to provide discontinuous nonadhesive bonds, and can comprise ultrasonic bonders or thermal bonders. For example, the side panel strips 118 can be transported between a rotary ultrasonic horn and an anvil roll, which devices are positioned on each side of the process at the cross machine direction location of the fastening components 82, 84 and 83, 85. Particular ultrasonic bond patterns comprising individual, circular bonds which are compatible with mechanical fastening materials are disclosed in U.S. Pat. 5,660,666 issued Aug. 26, 1997 to Dilnik et al., which is incorporated herein by reference. The fastening components 82–85 can be maintained on the side panel strips 118 until reaching the bonding devices 180 with suitable vacuum devices (not shown), or can be attached to the side panel strips at the fastener application station 150 with adhesive bonds. For secure attachment, it may be desirable to attach the fastening components with both adhesive and discontinuous nonadhesive bonds. Suitable attachment adhesives are available from commercial vendors such as Findley Adhesive, Inc., Wauwatosa, Wis. U.S.A.

Because the first and second fastening components 82–85 are disposed at the same selected cross machine direction locations, a pair of bonding devices 180 disposed on opposite sides of the machine center line and at the same selected cross machine direction locations as the fastening components is all that is needed to bond all of the fastening components to the side panel strips 118. Each bonding device 180 can be activated either continuously or intermittently to bond a second fastening component 84 or 85 followed by a first fastening component 82 or 83 to each side panel strip 118 (FIG. 2). Alternatively, of course, the location of the fastening components could be reversed such that each bonding device 180 would initially bond a first fastening component 82 or 83 and would subsequently bond a second fastening component 84 or 85 to each side panel strip.

The bonding devices 180 can form a regular or irregular pattern of discontinuous nonadhesive bonds that permanently bond the fastening components to the side panel strips 118. Each bonding device 180 thus defines an operative bonding width, which for purposes of the present invention is the width of the resulting nonadhesive bonding pattern measured parallel to the cross machine direction. The operative bonding widths of the bonding devices 180 can be equal to the width dimension of the first fastening components 82 and 83 and/or the second fastening components 82 and 83, measured parallel to the cross machine direction. Alternatively, the operative bonding widths of the bonding devices 180 can be greater than the width dimension of the first fastening components 82 and 83 and/or the second fastening components 82 and 83, in which case additional portions of the side panel strips 118 transversely inward and/or outward from the fastening components may have bond points formed therein. Still alternatively, the operative bonding widths of the bonding devices 180 can be less than the width dimension of the first fastening components 82 and 83 and/or the second fastening components 82 and 83, in which case the bonding devices 180 may not bond the entire width dimension of the fastening components to the side panel strips 118. The bonding devices 180 can have the same or different operative bonding widths.

As noted above, the first and second fastening components 82–85 can be disposed at the same selected cross machine direction locations, and the bonding devices 180 can also be disposed at the same selected cross machine direction locations as the fastening components. In this case, the fastening components 82–85 will be bonded to the side panel strips 118, and may be bonded over their full width provided the operative bonding width is equal to or greater than the width dimension of the fastening components. Other embodiments can also be effective to bond the fastening components 82–85 in place with a minimal number of bonding devices 180. For example, the first fastening components 82 and 83 can be disposed at selected first cross machine direction locations and the second fastening components 84 and 85 can be disposed at selected second cross machine direction locations. Provided the selected first cross machine direction locations and the selected second cross machine direction locations are separated from one another by less than the operative bonding width, the bonding devices 180 can be positioned such that at least portions of each of the fastening components 82–85 will be bonded to the side panel strips 118. More particularly, the bonding devices 180 can be disposed at selected cross machine direction locations such that the operative bonding widths overlap at least part of the first cross machine direction locations and at least part of the second cross machine direction locations. In particular embodiments, the selected first cross machine direction locations can overlap to some degree the selected second cross machine direction locations, wherein selected portions of the first fastening components 82 and 83 are at the same cross machine direction locations as selected portions of the second fastening components 84 and 85.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82–85 and the side panel material 116 when the side panel material 116 reaches a particular machine direction 108 location. In one particular embodiment, the target areas correspond to portions of the fastening components 82–85 near the waist edges 38 and 39. The bonding devices 180 can be registered to provide a relatively higher degree of bonding which begins while disposed on one fastening component (such as 84 in FIG. 2), continues through the region where the product assemblage 113 will subsequently be cut (see cut line 159 in FIG. 2), and ends after being disposed on another fastening component (such as 82). Alternatively, the bonding devices 180 can destroy engaging elements of the fastening components 82–85 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 5 and 6). To this end, the assembly section 100 can include a die cutting roll 182 and a backing roll 184. In the illustrated embodiment, a portion of each strip 118 is trimmed from the trailing edge 154 (FIG. 2) in order to form the angled and/or curved leg end edges 70 in the back waist region 24.

The method and apparatus to this point provides a continuous web of interconnected and partially assembled training pants moving in the direction indicated by arrow 108. This continuously moving product assemblage 113 can be passed through a cutter 186 which selectively cuts the web through each pair of opposed side panel strips 118 into discrete, partially assembled training pants 102. Such cutters 186 are generally known to those skilled in the art and can include, for example, the combination of a cutting roll 187 and an anvil roll 188 through which the web travels. The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

The discrete training pants 102 can then be folded using any suitable folding mechanism 202, such as blade folders, linear folders, book folders, tucker blades or the like. The specific type selected for a given application may depend upon the type of garment being manufactured and whether the garment is to be prefastened in a pant configuration. In general, the training pants 102 can be folded about a fold line generally bisecting the training pants. As such, the waist regions 22 and 24 of each training pant 102 are positioned in facing relationship with the side panels 34 and 134 extending laterally outward relative to the longitudinal axis 48 of the training pant. The fold line can extend in a lateral direction through the crotch region 26 of the training pant. Desirably, each discrete training pant 102 is consistently folded about the fold line such that the front and back waist edges 38 and 39 of the training pant align with each other. Particular methods and apparatus for maintaining separation of the side panels and fastening components during folding are disclosed in U.S. Pat. Application Ser. No. unknown, filed on May 15, 2001 by J. D. Coenen et al. and titled "Folding And Manufacture Of Pants," which is incorporated herein by reference.

A portion of a continuously moving product assemblage 113 depicting an alternative method according to the present invention is illustrated in FIG. 3. The illustrated product assemblage 113 reflects a position immediately following the fastener application station 150. The illustrated product assemblage comprises first and second continuous layers 300 and 302 with discrete absorbent assemblies 114 disposed between the first and second layers. The first layer 300 has relatively wider portions defining integral side panel strips 118. The side panel strips 118 extend transversely outward from the longitudinal center line 105 of the product assemblage 113 on both sides of the longitudinal center line to form pairs of opposed side panel strips. The plurality of pairs of opposed side panel strips 118 are spaced from one another in the machine direction 108.

According to the present embodiment, each side panel strip 118 defines a leading edge 152, a leading zone 310 disposed adjacent the leading edge, a trailing edge 154 spaced from the leading edge in the machine direction 108, a trailing zone 312 disposed between the trailing edge and the leading zone, and a distal edge 156. Dashed lines 159 illustrate the locations at which the product assemblage 113 can subsequently be cut to provide the discrete training pants 102. When the assemblage 113 is cut, the leading zones 310 form side panels of one training pant and the associated trailing zones 312 form side panels of the subsequent training pant.

The first fastening components 82 and 83 can be positioned on and bonded to the side panel strips 118, and in the illustrated embodiment are positioned on and bonded to the underside of the side panel strips. The first fastening components 82 and 83 can be disposed on opposite sides of the longitudinal center line 105 at selected cross machine direction locations, marked generally by arrows 320, but it should be understood that the cross machine direction locations also encompass the cross machine direction width of the fastening components 82 and 83. Additionally, the first fastening components 82 and 83 can be disposed in one of the leading zone 310 or the trailing zone 312. In the illustrated embodiment, the first fastening components 82 and 83 are offset in the machine direction 108 relatively closer to the leading edge 152 than the trailing edge 154, so as to be disposed in the leading zones 310. The pants 102 could alternatively be constructed with the first fastening components disposed in the trailing zones 312 (not shown).

Subsequent to positioning the first fastening components 82 and 83, the product assemblage 113 is processed through a pair of bonding devices 180. The individual bonding devices 180 can be disposed on opposite sides of the machine center line at selected cross machine direction locations. The cross machine direction location of each bonding device 180 can be selected so that its operative bonding width overlaps at least partially the cross machine direction location 320 of the respective first fastening components 82 or 83. In particular embodiments, the individual bonding devices 180 can be disposed at the same selected cross machine direction locations 320 as the first fastening components 82 and 83. The bonding devices 180 can be activated at machine direction 108 positions which correspond to the leading zones 310 to bond the first fastening components 82 and 83 to the side panel strips 118 with a pattern of discontinuous nonadhesive bonds. In addition, the bonding devices 180 can be activated at machine direction 108 positions which correspond to the trailing zones 312 to form second fastening components 84 and 85 in the trailing zones.

Figure 7:
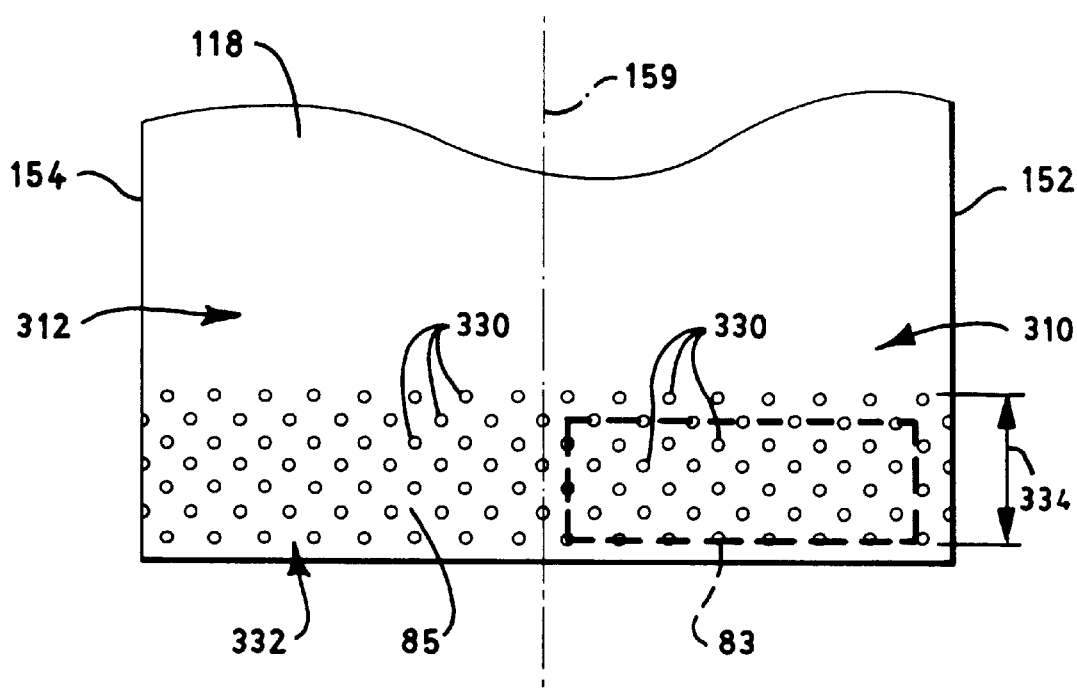
FIG. 7 illustrates an enlarged portion of a side panel strip of the product assemblage shown in FIG. 3.

With additional reference to FIG. 7, the bonding devices 180 create discontinuous nonadhesive bonds 330 in discrete and defined portions 332 of the trailing zones 312. The defined portions 332 and hence the second fastening components 84 and 85 have a cross machine direction width dimension equal to the operative bonding width. The operative bonding width can be greater than, equal to, or less than the width dimension of the first fastening components, and is illustrated in FIG. 7 by arrow 334 as slightly larger than the width of the fastening component 83. The discontinuous nonadhesive bonds 330 can comprise any shape providing less than 100 percent bond area, such as rectangles, bars, non-square bars, ovals, circles, dots, curved or straight lines, diamonds, other geometric shapes, irregular shapes, or the like, and including combinations and regular or irregular intersecting or nonintersecting patterns thereof. As illustrated, the discrete portions 332 can comprise spaced apart point bonds which form visually distinguishable regions for attachment of the fastening components. The discontinuous nonadhesive bonds 330 can modify the integrity characteristics of the trailing zones 312 for better performance as fastening components 84 and 85, and in particular can provide improved strength of stretchable side panel materials.

Hence, the bonding devices 180 can provide discontinuous nonadhesive bonds 330 that not only bond the first fastening components 82 and 83 to the side panel strips 118 but also create discrete and defined portions 332 that function as second fastening components 84 and 85. The second fastening components 84 and 85 can be formed at the same selected cross machine direction locations 320 as the first fastening components 82 and 83. Alternatively, the bonding devices 180 can be disposed at selected cross machine direction locations, and/or the operative bonding widths can be selected, such that the operative bonding widths only partially overlap the cross machine direction locations of the first fastening components 82 and 83. This product assemblage 113 can thereafter be passed through a cutter 186 (FIG. 1), which selectively cuts the web through each pair of opposed side panel strips 118 between the leading and trailing zones 310 and 312 to form a plurality of into discrete, partially assembled training pants 102.

The present method can provide a garment 102 with refastenable fastening components 82–85. The garment 102 can include a chassis 32 defining a first waist region with opposed first side panels, a second waist region with opposed second side panels, and a crotch region disposed between and interconnecting the first and second waist regions. The first fastening components 82 and 83 can be disposed on the first side panels and bonded to the first side panels with discontinuous nonadhesive bonds 330. The second fastening components 84 and 85 can be formed in the second side panels. Each second fastening component can comprise a discrete portion 332 of a second side panel having discontinuous nonadhesive bonds 330 formed therein. The discrete portions 332 can be refastenably engageable with the first fastening components 82 and 83. It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of making garments with fastening components, comprising:

transporting a continuous product assemblage in a machine direction, the product assemblage defining opposite first and second major surfaces;

positioning first fastening components on the first major surface, the first fastening components disposed on opposite sides of a machine center line, the first fastening components disposed at selected first cross machine direction locations;

positioning second fastening components on the second major surface, the second fastening components being refastenably engageable with the first fastening components, the second fastening components disposed on opposite sides of the machine center line, the second fastening components disposed at selected second cross machine direction locations;

subsequent to positioning the first and second fastening components, processing the product assemblage through a pair of bonding devices, the bonding devices disposed on opposite sides of the machine center line, each bonding device defining an operative bonding width, the bonding devices disposed at selected cross machine direction locations such that the operative bonding widths overlap at least part of the first cross machine direction locations and at least part of the second cross machine direction locations;

activating each bonding device such that each bonding device bonds both a first fastening component to the product assemblage and a second fastening component to the product assemblage; and cutting the product assemblage at spaced locations to form a plurality of discrete garments with fastening components.

2. The method of claim 1, wherein the first cross machine direction locations are the same as the second cross machine direction locations.

3. The method of claim 1, wherein the first cross machine direction locations overlap the second cross machine direction locations.

4. The method of claim 1, wherein the respective first cross machine direction locations and second cross machine direction locations are separated from one another by an amount less than the operative bonding width of the respective bonding devices.

5. The method of claim 1, wherein the bonding devices are disposed at the same selected cross machine direction locations as the first fastening components.

6. The method of claim 2, wherein the bonding devices are disposed at the same selected cross machine direction locations as the first fastening components.

7. The method of claim 1, wherein the first and second fastening components each define a width dimension, and the operative bonding widths are equal to or greater than the width dimension of each of the first and second fastening components.

8. The method of claim 1, wherein the first and second fastening components each define a width dimension, and the operative bonding widths are less than the width dimension of at least one of the first and second fastening components.

9. The method of claim 1, wherein the bonding devices form a plurality of spaced apart point bonds.

10. The method of claim 1, wherein the bonding devices comprise ultrasonic bonding devices.

11. The method of claim 1, wherein the bonding devices comprise thermal bonding devices.

12. The method of claim 1, wherein the first fastening components comprise loop type fasteners disposed on an inner surface and the second fastening components comprise hook type fasteners disposed on an outer surface, and the first fastening components are sized larger than the second fastening components.

13. The method of claim 1, wherein the first fastening components comprise loop type fasteners disposed on an outer surface and the second fastening components comprise hook type fasteners disposed on an inner surface, and the first fastening components are sized larger than the second fastening components.

14. A method of making garments with mechanical fastening components, comprising:

transporting a continuous product assemblage in a machine direction, the product assemblage defining a longitudinal center line and opposite first and second major surfaces, the product assemblage comprising a plurality of pairs of opposed side panel strips, each pair comprising a side panel strip extending transversely outward from the longitudinal center line on both sides of the longitudinal center line, the plurality of pairs of opposed side panel strips being spaced from one another in the machine direction;

positioning first fastening components on the first major surface of each pair of opposed side panel strips, the first fastening components disposed on opposite sides of the longitudinal center line, the first fastening components disposed at selected first cross machine direction locations;

positioning second fastening components on the second major surface of each pair of opposed side panel strips, the second fastening components being refastenably engageable with the first fastening components, the second fastening components disposed on opposite sides of the longitudinal center line, the second fastening components disposed at selected second cross machine direction locations, the second fastening components being spaced in the machine direction from the first fastening components;

subsequent to positioning the first and second fastening components, processing the product assemblage through a pair of bonding devices, the bonding devices disposed on opposite sides of the machine center line, each bonding device defining an operative bonding width, the bonding devices disposed at selected cross machine direction locations such that the operative bonding widths overlap at least part of the first cross machine direction locations and at least part of the second cross machine direction locations;

activating each bonding device such that each bonding device bonds both a first fastening component to the side panel strips and a second fastening component to the side panel strips; and cutting the product assemblage through each pair of opposed side panel strips to form a plurality of discrete garments, each discrete garment defining a first waist region comprising opposed side panels, a second waist region comprising opposed side panels, and an interconnecting region disposed between and interconnecting the first and second waist region, the first fastening components disposed on the side panels in the first waist region, and the second fastening components disposed on the side panels in the second waist region.

15. The method of claim 14, wherein the first cross machine direction locations are the same as the second cross machine direction locations.

16. The method of claim 14, wherein the first cross machine direction locations overlap the second cross machine direction locations.

17. The method of claim 14, wherein the respective first cross machine direction locations and the second cross machine direction locations are separated from one another by an amount less than the operative bonding width of the respective bonding device.

18. The method of claim 14, wherein the bonding devices are disposed at the same selected cross machine direction locations as the first fastening components.

19. The method of claim 15, wherein the bonding devices are disposed at the same selected cross machine direction locations as the first fastening components.

20. The method of claim 14, wherein the first and second fastening components each define a width dimension, and the operative bonding widths are equal to or greater than the width dimension of each of the first and second fastening components.

21. The method of claim 14, wherein the first and second fastening components each define a width dimension, and the operative bonding widths are less than the width dimension of at least one of the first and second fastening components.

22. The method of claim 14, wherein the side panel strips comprise an elastomeric material capable of stretching in a direction generally perpendicular to the machine direction.

23. The method of claim 22, wherein the elastomeric material comprises a laminate material formed of at least one elastomeric layer and at least one nonwoven layer.

24. The method of claim 14, wherein the product assemblage comprises a layer having relatively wider portions defining integral side panel strips.

25. The method of claim 14, wherein the product assemblage comprises discrete side panel strips attached to a continuous layer.

26. The method of claim 14, wherein the bonding devices form a plurality of spaced apart point bonds.

27. The method of claim 14, wherein the side panel strips are transported between a rotary ultrasonic horn and an anvil roll on each side of the machine center line at the same cross machine direction locations as the first and second fastening components.

28. The method of claim 14, wherein the bonding devices provide timed, non-uniform bonding of the fastening components to the side panel strips.

29. The method of claim 14, wherein positioning the first fastening components and the second fastening components comprises adhesively bonding the fastening components.

30. The method of claim 14, wherein the first fastening components comprise loop type fasteners disposed on an inner surface and the second fastening components comprise hook type fasteners disposed on an outer surface, and the first fastening components are sized larger than the second fastening components.

31. The method of claim 14, wherein the first fastening components comprise loop type fasteners disposed on an outer surface and the second fastening components comprise hook type fasteners disposed on an inner surface, and the first fastening components are sized larger than the second fastening components.

32. The method of claim 14, wherein the garments are disposable absorbent articles.

33. The method of claim 32, wherein the disposable absorbent articles are training pants.

34. A method of making garments with fastening components, comprising:

transporting a continuous product assemblage in a machine direction, the product assemblage defining a longitudinal center line, the product assemblage comprising a plurality of pairs of opposed side panel strips, each pair comprising a side panel strip extending transversely outward from the longitudinal center line on both sides of the longitudinal center line, the plurality of pairs of opposed side panel strips being spaced from one another in the machine direction, each side panel strip defining a leading edge, a leading zone disposed adjacent the leading edge, a trailing edge spaced from the leading edge in the machine direction, and a trailing zone disposed between the trailing edge and the leading zone;

positioning first fastening components on each pair of opposed side panel strips, the first fastening components disposed in one of the leading zone or the trailing zone, the first fastening components disposed on opposite sides of the longitudinal center line, the first fastening components disposed at selected first cross machine direction locations;

subsequent to positioning the first fastening components, processing the product assemblage through a pair of bonding devices, the bonding devices disposed on opposite sides of the machine center line, each bonding device defining an operative bonding width, the bonding devices disposed at selected cross machine direction locations such that the operative bonding widths overlap at least part of the first cross machine direction locations;

activating each bonding device such that each bonding device bonds a first fastening component to the side panel strips and each bonding device forms a second fastening component in the other of leading zone or the trailing zone, each second fastening component comprising a discrete portion of the other of the leading zone or the trailing zone having discontinuous nonadhesive bonds formed therein, the discrete portions being refastenably engageable with the first fastening components, the discrete portions disposed at selected second cross machine direction locations which overlap at least part of the first cross machine direction locations; and cutting the product assemblage through each pair of opposed side panel strips between the leading and trailing zones to form a plurality of discrete garments, each discrete garment defining a first waist region comprising opposed side panels, a second waist region comprising opposed side panels, and an interconnecting region disposed between and interconnecting the first and second waist region, the first fastening components disposed on the side panels in the first waist region, and the second fastening components disposed on the side panels in the second waist region.

35. The method of claim 34, wherein the first cross machine direction locations are the same as the second cross machine direction locations.

36. The method of claim 34, wherein the first fastening components define a width dimension, and the operative bonding widths are equal to or greater than the width dimension of the first fastening components.

37. The method of claim 34, wherein the first fastening components each define a width dimension, and the operative bonding widths are less than the width dimension of the first fastening components.

38. The method of claim 34, wherein the side panel strips comprise an elastomeric material capable of stretching in a direction generally perpendicular to the machine direction.

39. The method of claim 38, wherein the elastomeric material comprises at least one elastomeric layer and at least one nonwoven layer.

40. The method of claim 34, wherein the product assemblage comprises a layer having relatively wider portions defining integral side panel strips.

41. The method of claim 34, wherein the product assemblage comprises discrete side panel strips attached to a continuous layer.

42. The method of claim 34, wherein the side panel strips are transported between a rotary ultrasonic horn and an anvil roll on each side of the machine center line at the same cross machine direction locations as the first fastening components.

43. The method of claim 34, wherein the bonding devices form a plurality of spaced apart point bonds.

44. The method of claim 43, wherein the bonding devices comprise ultrasonic bonding devices.

45. The method of claim 43, wherein the bonding devices comprise thermal bonding devices.

46. The method of claim 34, wherein the first fastening components comprise hook type fasteners.

47. The method of claim 34, wherein the garments are disposable absorbent articles.

48. The method of claim 47, wherein the disposable absorbent articles are training pants.

* * * * *